(12) United States Patent
Allen et al.

(10) Patent No.: US 10,031,912 B2
(45) Date of Patent: Jul. 24, 2018

(54) VERIFICATION OF NATURAL LANGUAGE PROCESSING DERIVED ATTRIBUTES

(71) Applicant: International Business Machines Corporation, Armonk, NY (US)

(72) Inventors: Corville O. Allen, Morrisville, NC (US); Roberto Delima, Apex, NC (US); Thomas J. Eggebraaten, Rochester, MN (US); John E. Petri, St. Charles, MN (US); Marie L. Setnes, Bloomington, MN (US); Patrick M. Wildt, Morgan, MN (US)

(73) Assignee: International Business Machines Corporation, Armonk, NY (US)

( * ) Notice: Subject to any disclaimer, the term of this patent is extended or adjusted under 35 U.S.C. 154(b) by 113 days.

(21) Appl. No.: 14/584,414

(22) Filed: Dec. 29, 2014

(65) Prior Publication Data

US 2016/0188535 A1 Jun. 30, 2016

(51) Int. Cl.
*G06F 17/27* (2006.01)
*G06F 17/30* (2006.01)
*G16H 10/60* (2018.01)

(52) U.S. Cl.
CPC .... *G06F 17/30011* (2013.01); *G06F 17/2785* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 2012/0078062 A1* | 3/2012 | Bagchi | A61B 5/00 600/300 |
| 2013/0019286 A1* | 1/2013 | Barborak | G06F 17/27 726/4 |
| 2013/0033008 A1 | 12/2013 | Zadeh | |
| 2014/0143881 A1 | 5/2014 | Boday et al. | |
| 2014/0188462 A1 | 7/2014 | Zadeh | |
| 2014/0201126 A1 | 7/2014 | Zadeh et al. | |
| 2014/0280112 A1* | 9/2014 | Cheng | G06F 17/3053 707/728 |
| 2014/0365232 A1* | 12/2014 | Sadeghi | G06F 19/345 705/2 |

\* cited by examiner

*Primary Examiner* — Kevin Ky
(74) *Attorney, Agent, or Firm* — Gero G. McClellan

(57) ABSTRACT

System, method, and computer program product to identify candidate values to provide to a deep question answering (QA) system as part of a case, by receiving a case, wherein the case includes a plurality of documents for evaluation by the deep QA system, evaluating the plurality of documents using natural language processing (NLP) to identify one or more concepts reflected by text content within the plurality of documents in the case, wherein the plurality of documents includes a plurality of distinct values for at least a first one of the concepts, selecting, from the plurality of distinct values, a candidate value for the first concept to provide to the deep QA system to process the case, and prior to submitting the case to the deep QA system, returning at least the candidate value selected for the first concept to present in a user interface.

15 Claims, 7 Drawing Sheets

Staging characteristics

Primary tumor size: [ 3.1 ] cm

Derived

FIG. 6A

Watson has discovered 4 tumor sizes ( 3.1 cm, 4 cm, 4 cm, 2 cm ).
Hover over each for more detail.

Watson is 85% confident this is the intended tumor size based on...
Procedure: Ultrasound ★★★★★
Size: 3.1 cm ★★★★
Date: 03/09/2012 ★★
You have previously indicated this *procedure is most important*.

Watson is 75% confident this is the intended tumor size based on...
Procedure: Mammogram ★★★★
Size: 4 cm ★★★
Date: 03/09/2012
2 colleagues you trust would choose this tumor size (see *who and why*).

Watson is 30% confident this is the intended tumor size based on...
Size: 2 cm ★★★

Watson is 50% confident this is the intended tumor size based on...
Size: 4 cm ★★★★
2 colleagues you trust would choose this tumor size (see *who and why*).

Dr. Benson
Alice Jorgensen

This is the largest tumor size mentioned.

FIG. 6B

VERIFICATION OF NATURAL LANGUAGE PROCESSING DERIVED ATTRIBUTES

BACKGROUND

Embodiments disclosed herein relate to computer software. More specifically, embodiments disclosed herein relate to computer software which identifies attributes derived from natural language processing.

Deep question answering (QA) systems answer questions by finding and evaluating candidate answers against a variety of machine learning, natural language processing, and other models generated from a corpus of relevant documents. To answer a given question, the QA system may identify a set of topics, features and attributes to evaluate using the models and content in the corpus. Questions may be posed in various forms and include reference information or notes. Concepts may be extracted from the reference information included in a question and evaluated along with the values associated with the concepts. In some cases, the question may be implicit, e.g., where the deep QA system is used to recommend a treatment for a given medical condition based on the electronic medical records of an individual. However, in some cases, there may be multiple values in the case notes for a given concept. What is needed is a technique for selecting values derived from natural language processing (NLP).

SUMMARY

Embodiments disclosed herein provide a system, method, and computer program product to identify candidate values to provide to a deep question answering (QA) system as part of a case, by receiving a case, wherein the case includes a plurality of documents for evaluation by the deep QA system, evaluating the plurality of documents using natural language processing (NLP) to identify one or more concepts reflected by text content within the plurality of documents in the case, wherein the plurality of documents includes a plurality of distinct values for at least a first one of the concepts, selecting, from the plurality of distinct values, a candidate value for the first concept to provide to the deep QA system to process the case, and prior to submitting the case to the deep QA system, returning at least the candidate value selected for the first concept to present in a user interface.

BRIEF DESCRIPTION OF THE SEVERAL VIEWS OF THE DRAWINGS

So that the manner in which the above recited aspects are attained and can be understood in detail, a more particular description of embodiments of the disclosure, briefly summarized above, may be had by reference to the appended drawings.

It is to be noted, however, that the appended drawings illustrate only typical embodiments of this disclosure and are therefore not to be considered limiting of its scope, for the disclosure may admit to other equally effective embodiments.

FIGS. 6a and 6b illustrate a UI for selecting candidate values for a deep QA system to use in generating a treatment recommendation, according to one embodiment.

DETAILED DESCRIPTION

Figure 1:
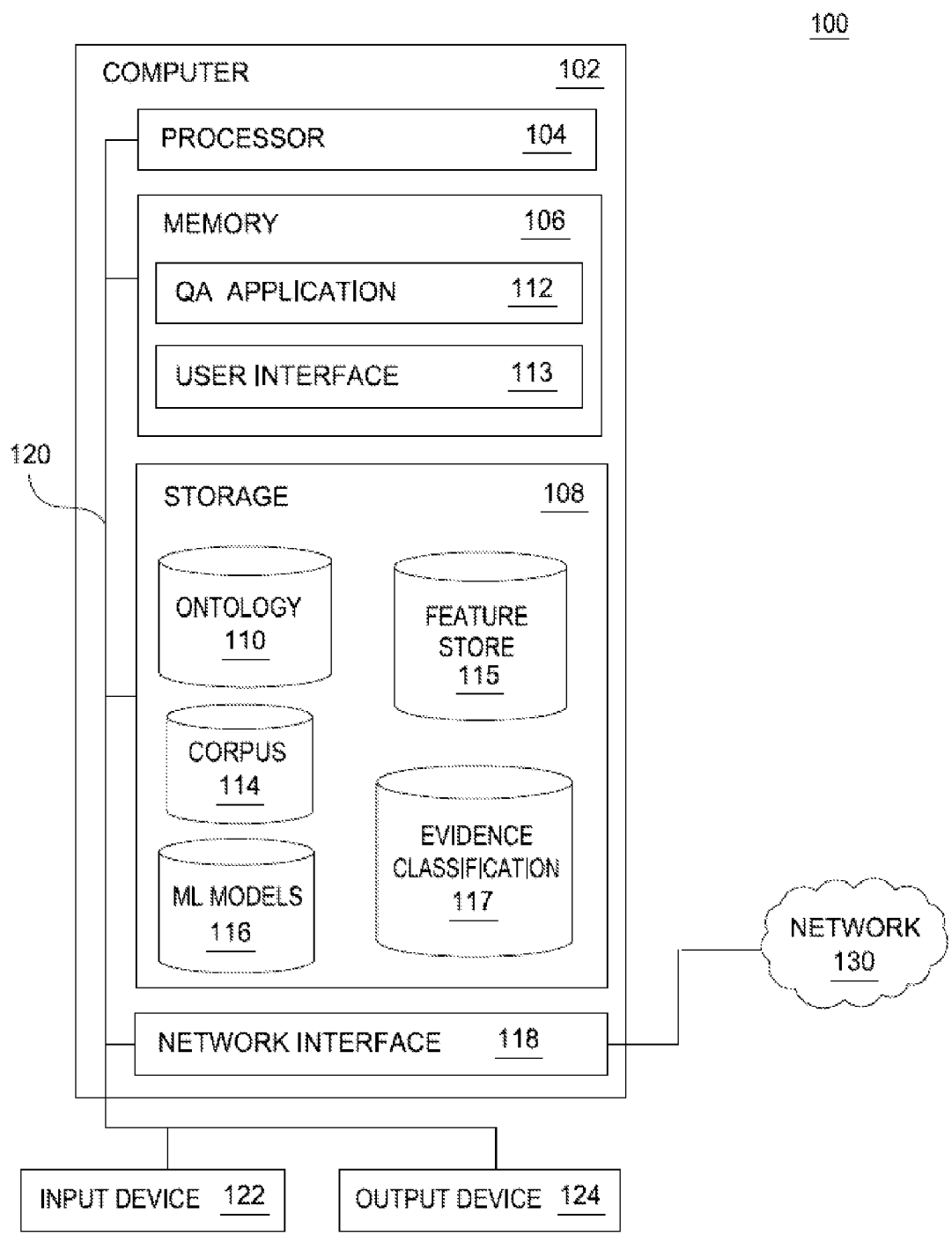
FIG. 1 is a block diagram illustrating a networked system for selecting candidate values for a deep QA system to use in generating a treatment recommendation according to one embodiment.

Embodiments disclosed provide techniques for selecting candidate values used by a deep QA system to generate a treatment recommendation. The need to select the most useful data for a given attribute is highlighted in automated systems which can generate treatment recommendations using machine learning and other techniques to evaluate data from an electronic medical record. For example, a system for selecting candidate values for a deep QA system to use in generating a treatment recommendation, such as IBM's Watson, may be tasked to process a case note entered by a doctor.

A case note presented to Watson may reference a concept, such as a tumor size or creatinine clearance level, which are then used to identify appropriate responses and treatments. Some concepts in the case notes may have multiple values. For example, during a course of treatment, a tumor may be measured multiple times on different days using a variety of procedures, such as via an ultrasound or mammogram, at different labs, or, after successful treatment to reduce/remove the tumor, all of which could result in varying measurements. A case note may contain an entry indicating that an ultrasound measured a tumor at 3.1 cm. The same case note may also indicate that a mammogram measured the tumor at 4 cm. Further, the case note may indicate that the ultrasound measurement is more recent and occurred after treatment. Thus, the case note includes the concept of a tumor size with two values, 3.1 cm and 4 cm, as well as attributes for each value. For example, the attributes related to how the values were determined, the ultrasound and mammogram, as well as the dates the values were determined.

In one embodiment, the QA system evaluates the case note, to select candidate values for processing, select a value for a concept from the patient data, process the concepts and ultimately recommend a treatment. To do so, the QA system determines which attributes are preferred attributes. That is, it is preferable that the "best" instance of each concept values in the case note be used to evaluate a case note. Thus, a QA system needs to identify which instance of a concept to use when generating a recommendation. One system to provide such values could simply prompt a user to provide each value one by one. However, requiring users to manually select and review each concept and value reduces effectiveness and user acceptance. Alternatively, if the QA system does not pick the correct values for concepts, the quality of the recommendations suffers. In such environments, selecting candidate values for a deep QA system to use in generating a treatment recommendation is valuable.

A system may select candidate values for a deep QA system to use in generating a treatment recommendation through an analysis "pipeline" as a part of an overall QA system. A typical pipeline may begin with question analysis, which analyzes and annotates the case note to identify key concepts upon which a search may be conducted. In addition, the system may identify candidate values of the concepts, especially in cases where they may be multiple candidates (such as in tumor size measurements). The next step of the pipeline may include evaluating the concepts and candidate values from the case using a trained model to determine a confidence score for the candidate value. The pipeline may then select a value from the candidate values, which the UI component may then present to the user. The UI component may also include elements which allow the user to correct or modify the selected value. A pipeline may represent the execution of various analysis programs, or engines, on both the case note text and candidate answers (i.e., text passages extracted from documents in a corpus) in order to deduce a probable correct answer.

Pipelines may be created for each domain or problem space (e.g. a different pipeline used for supporting treatment for different medical conditions,). In fact, analysis engines themselves may be unique to a particular domain (e.g., identification of a tumor stage or size, identification of drugs, potential drug interactions, etc.). Question and answer analysis within a pipeline may also include complex natural language processing algorithms, used, for example, to identify deep semantic relationships within the text. The scoring phase of a deep question answer (QA) system, such as IBM's Watson, may call various scoring algorithms to help determine a correct answer to a case. A scoring algorithm may generate one or more feature scores to indicate how confident it is in its answer. The deep QA system may also use a training phase to learn which features, or combinations of features, are best at predicting the right answers for different types of questions. Once the deep QA system has been trained, subsequent cases or questions presented to the pipeline may use the machine-learned model to generate most likely correct answer.

FIG. 1 is a block diagram illustrating a networked system 100 for selecting candidate values for a deep QA system to use in generating a treatment recommendation according to one embodiment. The networked system 100 includes a computer 102. The computer 102 may also be connected to other computers via a network 130. In general, the network 130 may be a telecommunications network and/or a wide area network (WAN). In a particular embodiment, the network 130 is the Internet.

The computer 102 generally includes a processor 104 connected via a bus 120 to a memory 106, a network interface device 118, a storage 108, an input device 122, and an output device 124. The computer 102 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single identity, it should be understood that the memory 106 may comprise a plurality of modules, and that the memory 106 may exist at multiple levels, from high speed registers and caches to lower speed but larger DRAM chips. The network interface device 118 may be any type of network communications device allowing the computer 102 to communicate with other computers via the network 130.

The storage 108 may be a persistent storage device. Although the storage 108 is shown as a single unit, the storage 108 may be a combination of fixed and/or removable storage devices, such as fixed disc drives, solid state drives, removable memory cards or optical storage. The memory 106 and the storage 108 may be part of one virtual address space spanning multiple primary and secondary storage devices.

As shown, the memory 106 contains a QA application 112 configured to operate a deep question answering (QA) system, and a user interface 113, which presents information to a user and allows for user interaction. One example of a deep question answering system is Watson, by the IBM Corporation of Armonk, N.Y. When a user submits a case (also referred to as a question), the QA application 112 provides an answer to the case based on an analysis of a corpus of information. The QA application 112 may execute a pipeline to generate a response to the case, which is returned to the user. The QA application 112 may further be configured to classify questions and identify concepts relevant to generate a correct response to the question. The QA application 112 may further be configured to identify attributes relevant to generating a correct response to the questions, and storing the resulting relationships for later use. The QA application 112 may further be configured to perform partial or parallel pipeline execution. For example, if a class of questions includes features highly correlated with a correctness of an answer (that is, substantially improves a predicted correctness of an answer) and a candidate answer for a question received by the QA application 112 does not contain the feature, the QA application 112 may skip processing that candidate answer to improve performance and conserve resources.

As shown, storage 108 contains an ontology 110, corpus 114, feature store 115, ML models 116, and evidence classification 117. The ontology 110 provides a structural framework for organizing information. An ontology formally represents knowledge as a set of concepts within a domain, and the relationships between those concepts. The corpus 114 is a body of information used by the QA application 112 to generate answers to cases. For example, the corpus 114 may contain scholarly articles, dictionary definitions, research data related to treatments, and the like. The QA application 112 may leverage predictive algorithms (or models) in order to generate candidate answers to speculative questions. Machine learning (ML) models 116, such as one using a logistical regression, are created by the QA application 112 during the training phase. Models may be trained based on examples to learn weights to associate with each attribute correlating with how predictive the attribute is of the value used for a concept in the training cases. ML models are used during a runtime pipeline to score and rank candidate values based on attributes previously found for each candidate value. Evidence classification 117 stores relationships between evidence from the corpus 114, the question context, and the predictive features. Although depicted as a database, ontology 110, corpus 114, feature store 115, ML models 116, and evidence classification 117 may take any form sufficient to store data, including text files, xml data files, and the like. In one embodiment, the ontology 110 is part of the corpus 114. Although depicted as a common computing system, any combination of the QA application 112, the ontology 110, corpus 114, feature store 115, ML models 116, and evidence classification 117 may reside on different computing systems as well.

The input device 122 provides input to the computer 102. For example, a keyboard and/or a mouse may be used. The output device 124 may be any device for providing output to a user of the computer 102. For example, the output device 124 may be any conventional display screen. Although shown separately from the input device 122, the output device 124 and input device 122 may be combined. For example, a display screen with an integrated touch-screen may be used.

Figure 2:
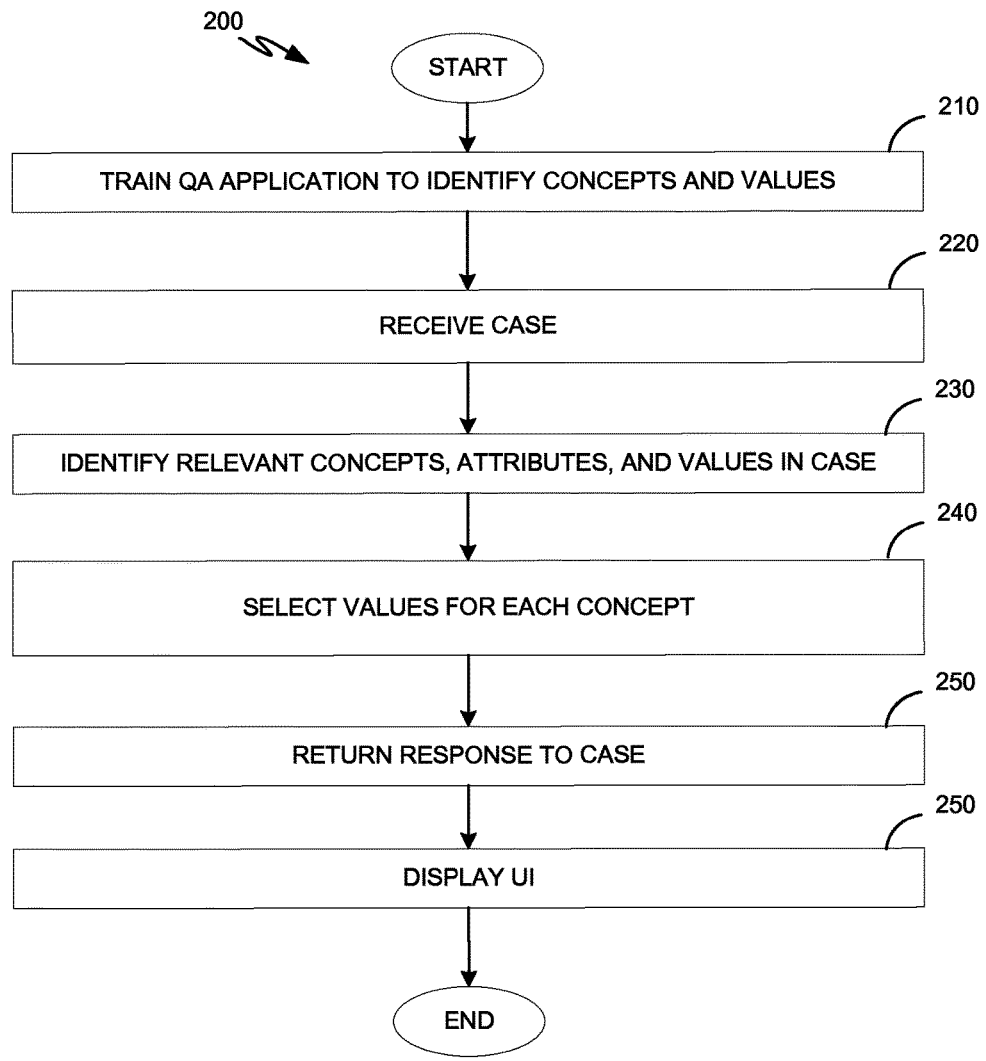
FIG. 2 is a flow chart illustrating a method for selecting candidate values for a deep QA system to use in generating a treatment recommendation, according to one embodiment.

FIG. 2 is a flow chart illustrating a method 200 for selecting candidate values for a deep QA system to use in generating a treatment recommendation, according to one embodiment. In one embodiment, the QA application 112 performs the steps of the method 200. At step 210, the QA application 112 is trained to identify concepts and values with relevant weights based on training cases. For example, during the training process, the QA application 112 identifies concepts for later use in medical logic processing, such as for generating a treatment recommendation. The QA application identifies concepts or combination of concepts used to process the case note. Models may be trained based on examples to learn features and relationships among features. Weights are accorded to various features and relationships based on how well those features and relationships correlate with example training cases and outcomes. When a subsequent case note is presented, the QA application 112 may then apply this model and examine how well the attributes in the case note fit the model. Step 210 is discussed in greater detail with reference to FIG. 3.

At step 220, the QA application receives the case note for processing. At step 230, the QA application 112 identifies the relevant concepts, attributes, and values in the case note. Generally, the QA application 112 evaluates the case note using any suitable method to identify the concepts, including natural language processing (NLP) to extract normalized terms and concepts from the case note. The QA application parses the case note to identify passages (typically unstructured text content). For example, NLP, may be used to determine whether the case note includes a concept. As noted, a case note may include multiple values for any identified concept or topic. For example, a tumor may have been measured multiple times during a course of treatment, with different measured sizes each time. Each measurement in the case note provides a candidate value for the concept to use in generating a treatment recommendation when the case is processed. Each value for a concept may include sets of attributes characterizing the value. For example, the date a value is observed, decisiveness of the language used for the observation, the importance or accuracy of the procedure undertaken to make the observation, and the size of the observation, in order to provide context for the value. More generally, each candidate value for a given concept may include a set of metadata characterizing each given candidate value. And this information may be present (or absent) for some of the values. For example, measurements obtained using one methodology may include certain information that is not obtained from other methodologies. In other cases, some elements of an EMR may simply be missing.

At step 240, the QA application 112 selects a value for each concept based on the trained model. At step 250, the QA application 112 returns a response to the case with identified concepts and values. At step 260, the user interface 113 organizes and displays the identified concepts and values to the user using a paper trail UI approach defined below.

Figure 3:
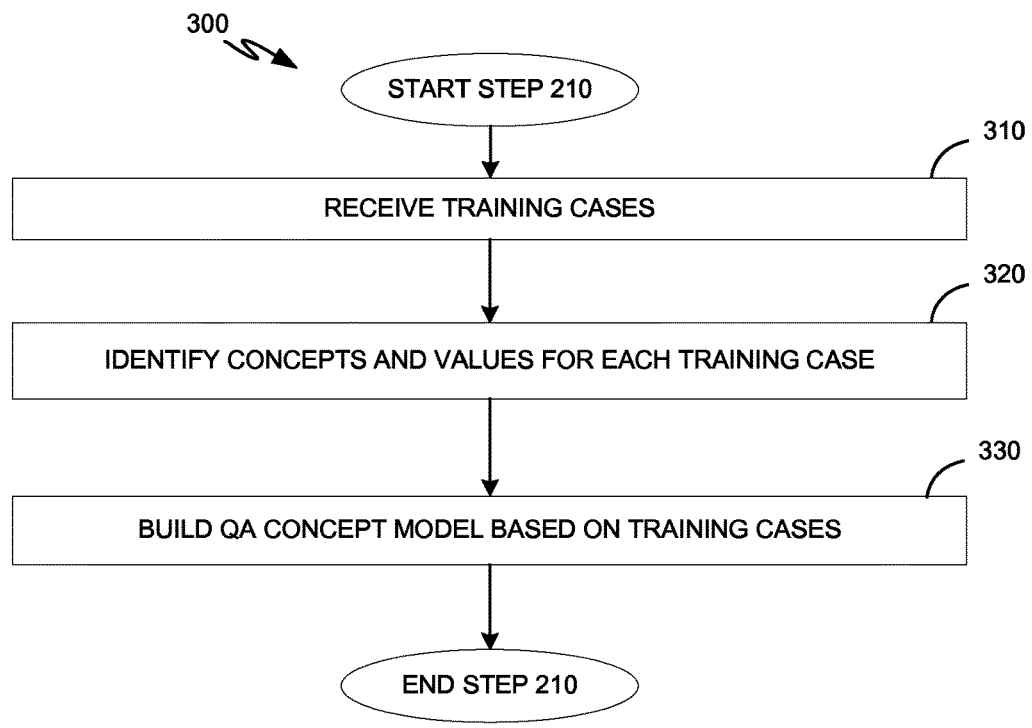
FIG. 3 is a flow chart illustrating a method for training a model for selecting candidate values for a deep QA system to use in generating a treatment recommendation, according to one embodiment.

FIG. 3 is a flow chart illustrating a method 300 for training a model for selecting candidate values for a deep QA system to use in generating a treatment recommendation, according to one embodiment. At step 310, the QA application 112 receives a collection of training cases used to train a model. A training case, for example, may be a case note used for training the model and may indicate a "most correct" answer or ranking of answers for each case. At step 320, the QA application 112 parses the received training case note to identify concepts, values, and attributes for each training case. The QA application 112 parses the case using any suitable method to identify the concepts, including natural language processing (NLP) to extract normalized terms to identify concepts as well as values and attributes related to the values. At step 330, the QA application builds the a concept model based on the identified concepts and attributes from the training cases. For example, logistical regression models may be trained based on examples to learn weights to associate with each attribute correlating with how predictive the attribute is of the "most correct" value for a concept in the training cases. The values for concepts in the training cases may be labeled to indicate the most correct value for a given concept. These weights allow the model to select a candidate value for the particular concept. In assigning weights, the model may learn from the context of values labeled as being most preferred in the training examples, the context of values not so labeled, as well as from the available metadata of each candidate in the case note. For example, attributes such as the date a particular observation is recorded, the decisiveness of the language used for the observation, the importance or accuracy of the procedure undertaken to make the observation, and the size of the observation may factor into weighting. The concept, attributes (including all relevant information used to classify the concept), as well as any associated predictive attributes, may be stored, for example to the feature classification 117, for later use.

Figure 4:
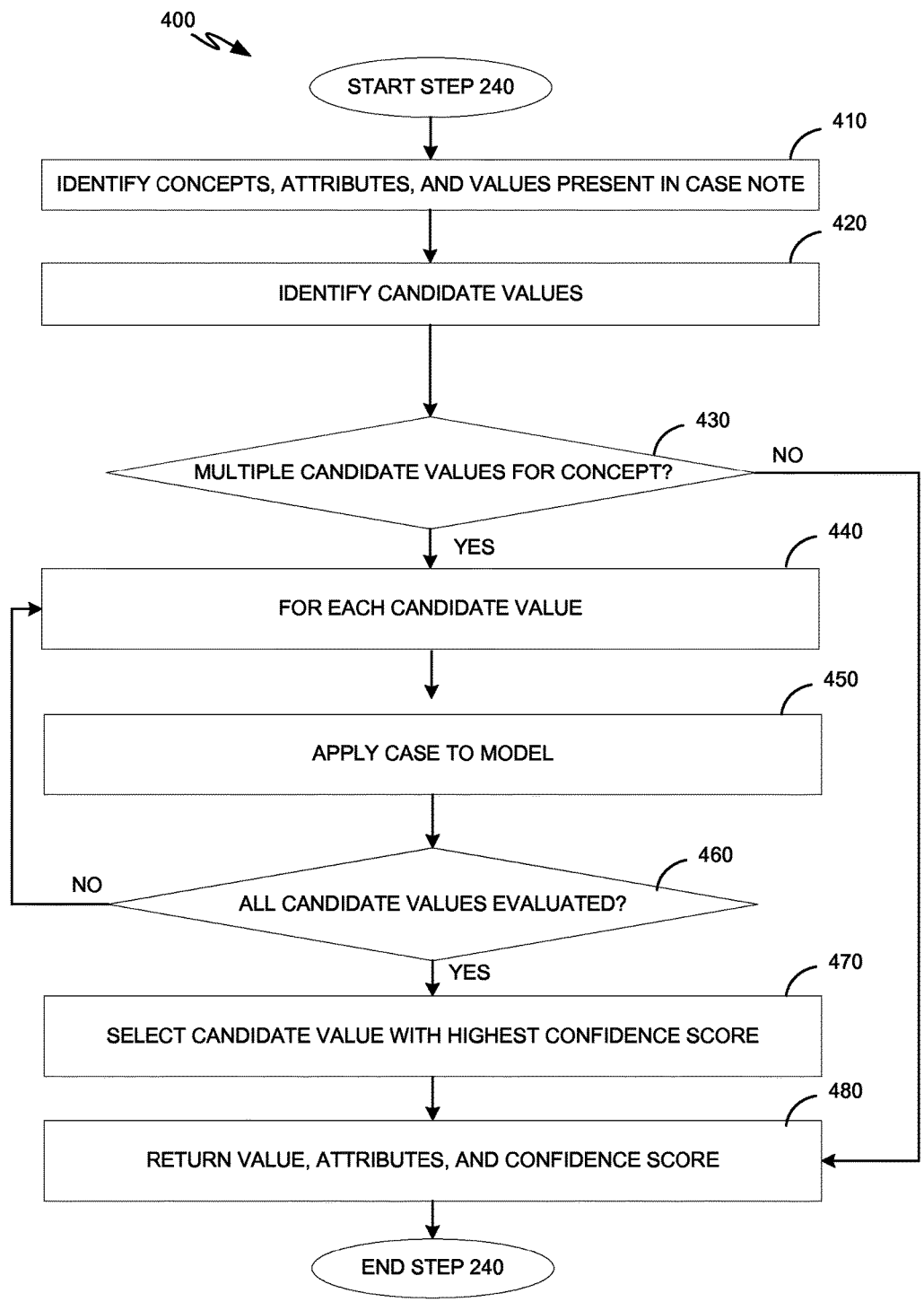
FIG. 4 is a flow chart illustrating a method for selecting candidate values for a deep QA system to use in generating a treatment recommendation, according to one embodiment.

FIG. 4 is a flow chart illustrating a method 400 for selecting candidate values for a deep QA system to use in generating a treatment recommendation, according to one embodiment. At step 410, the QA application 112 parses the received case note to identify concepts, attributes, and values for each case. The QA application 112 parses the case note using any suitable method to identify the concepts, including natural language processing (NLP) to extract normalized terms and concepts. At step 420, candidate values for each concept presented in the case are identified. For example, parsing a particular case may indicate that a concept of tumor size is present and that the attribute of measurement size has multiple instance values. That is, the tumor may have been measured multiple times using varying procedures and yielding different sizes, each of which is part of the case. Each measurement provides a potential value to select from the case note. Additionally attributes for the concepts are identified for each instance, such as the date of the measurement, the decisiveness of the language used in the case note, importance or accuracy of the procedure producing the value, and the size of the observation as attributes. As noted, these attributes generally correspond to the concepts and related attribute values included in the training examples use to build the model. At step 430, a determination is made as to whether multiple candidate values exist for a concept. If only a single candidate value exists, then that candidate value is selected and returned as the value for the concept. If multiple candidate values are present in the case note, then, at step 430, the QA application 112 may loop through steps including steps 440-460 for each candidate value. At step 450, the case note is applied to the model. The trained model takes into account the attributes associated with the candidate value as well as the context in which an attribute appears and generates a confidence score for each candidate value. After evaluating the set of candidate values (step 460), the candidate value with the highest confidence score is selected as the value for the concept at step 470 to use in generating a treatment recommendation from the case note. At step 480, the value, attributes, and confidence score for the value is returned. In one embodiment, the selected value along with other non-selected candidate values may be presented in a user interface prior to the case note being passed to the pipeline of the QA application for processing. This approach provides a paper trail of candidate values and gives the user an opportunity to select an alternative candidate value if they choose.

Figure 5:
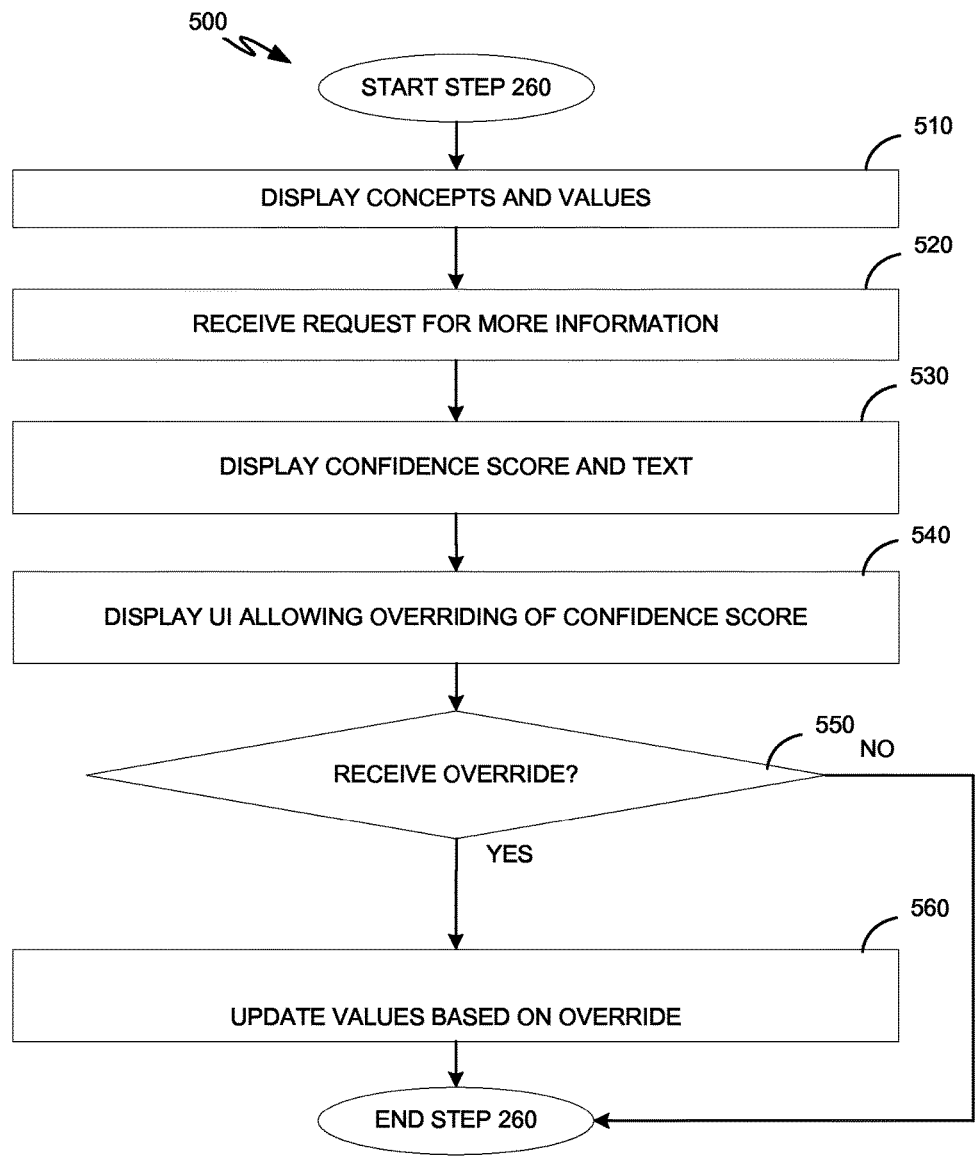
FIG. 5 is a flow chart illustrating a method for displaying a user interface for selecting candidate values for a deep QA system to use in generating a treatment recommendation, according to one embodiment.

FIG. 5 is a flow chart illustrating a method 500 for presenting candidate values selected for a deep QA system to use in generating a treatment recommendation, according to one embodiment. At step 510, the user interface 113 displays the concepts and values returned to the user in step 490. At step 520, the user requests more information about one of the values selected by the system. This request may be made by, for example, clicking a link, dropdown, or other UI element. At step 530, the UI may display confidence scores for the value and fragments of text related to the value. For example, UI may provide links to annotations considered in determining the value selected for a given concept. The UI may further display annotations in context with the text in which the annotation appeared. Doing so allows a user to quickly understand and verify the value selected by the QA application 112. The UI may also indicate the confidence score for the value selected for a given concept. The UI may also display icons for each value associated with attributes of the values, providing a user with information about how the value was determined and what the intensity or relative weight was. Such icons may reflect the confidence score. For example a number of stars may be displayed representative of the confidence score, where a greater number of stars are associated with a higher confidence. Further examples include a percentage or color-coded text.

At step 540, UI is displayed to the user. In one embodiment, the user may override the value for a given concept selected by the QA application. For example, when a user selects an UI element, the icons and text discussed above may be displayed. The UI may also display other values related to the concept that were not selected by the QA application. Once presented, the user can select a value for use by the QA application for generating treatment recommendations. For example, a trained model may prefer values associated with an attribute based on the precision offered by a particular test. However, the user may know that in this particular case, a particular attribute may not result in the optimum value. In such a case, the user can select which value from the case note to use in generating a treatment recommendation. At step 550, the UI waits to receive a confirmation of the values for use in generating treatment recommendations. Where the UI receives a confirmation, the method 500 ends. If the UI receives an override, the method proceeds to step 560 where the overridden values are updated with the user selected value and passed to the QA application to generate treatment recommendations. In one embodiment, the QA application may maintain a history storing information related to overrides received by the user. The UI may also display other users who have overridden the determined value as well as the value selected by the user. Displaying other users who have overridden the determined value provides a social aspect where the user may see the choices made by other users that they trust to help the user evaluate the values.

FIGS. 6a and 6b illustrate a UI for selecting candidate values for a deep QA system to use in generating a treatment recommendation, according to one embodiment. The user interface 600 displays concept 610 and selected value 615. UI element 620 allows the user to request more information about the attribute value 615 "3.1 cm" for the concept 610 "primary tumor size." Upon receiving a request to display more information, confidence scores 625 for the values 630, along with the attributes 635 may be displayed. The UI may also display icons 640 associated with attributes of the values. The UI may further display other users 645 who have selected a particular value or attribute. The UI may also display a prompt for users who have selected a particular value or attribute allowing the users to indicate why they selected the particular value or attribute. This UI may also display this reason 650.

Figure 7:
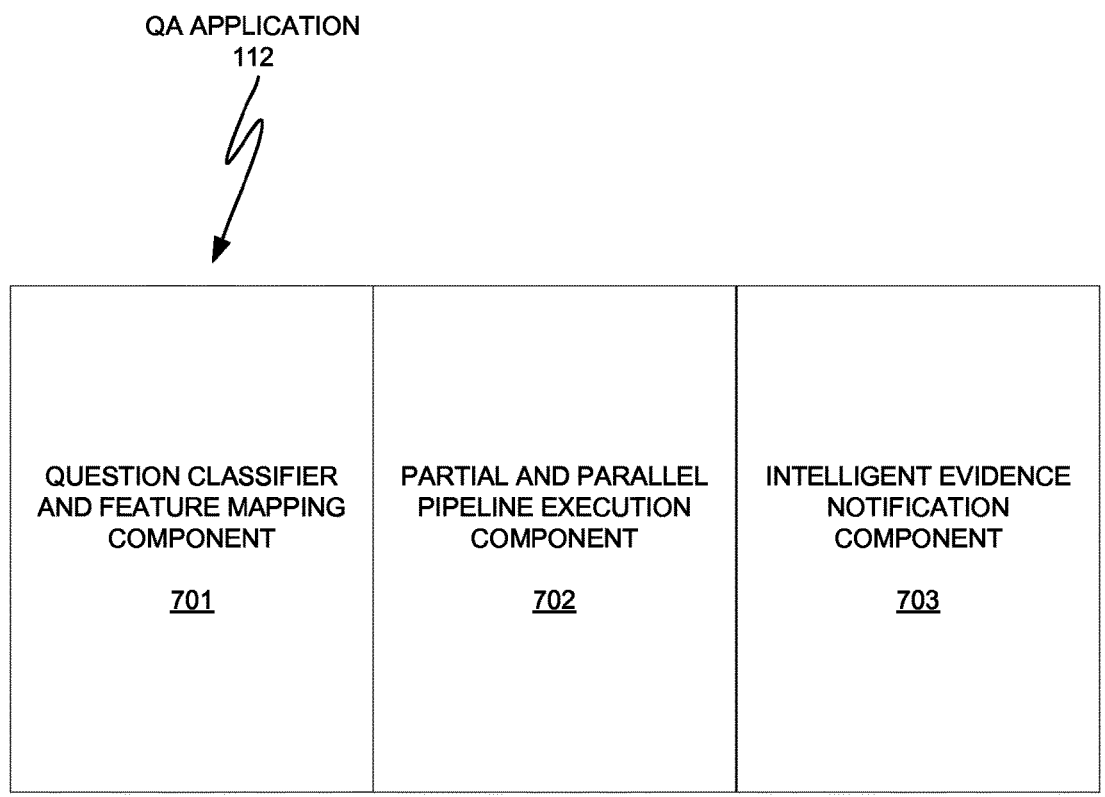
FIG. 7 is a block diagram illustrating components of a system for selecting candidate values for a deep QA system to use in generating a treatment recommendation.

FIG. 7 is a block diagram illustrating components of a system 700 for selecting candidate values for a deep QA system to use in generating a treatment recommendation. In one embodiment, the deep question answering system is the QA application 112. As shown, the QA application 112 contains a question classifier and feature mapping component 701, a partial and parallel pipeline execution component 702, and an attribute verification component 703. The question classifier and feature mapping component 701 may, during the training phase, classify questions based on type, and identify the features which are most highly relevant in generating a correct response to the questions in a training case. Once identified, the features may be stored in a feature store, such as feature store 115. The partial and parallel pipeline execution component 702 may, when presented with a subsequent case, access the dependencies defined in the feature store 115 to reduce processing of candidate answers that do not have the features identified as highly relevant to answering a particular class of question. The attribute verification component 703 may identify relevant attributes and monitor attributes of this type to determine whether they have been changed. Upon detecting a change, the attribute verification component 703 may determine whether the change in attribute preferences have an impact on the confidence of a response generated using the changed attribute. In such a scenario, the intelligent evidence notification component 703 may reprocess cases to determine whether the determined value has changed.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the preceding, reference is made to embodiments of the disclosure. However, it should be understood that the disclosure is not limited to specific described embodiments. Instead, any combination of the preceding features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be used. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access a deep question answering system or related data available in the cloud. For example, the deep question answering system could execute on a computing system in the cloud and provide question classification and feature mapping. In such a case, the deep question answering system could classify questions, map features and store the resultant data sets at a storage location in the cloud. Doing so allows a user to access this information from any computing system attached to a network connected to the cloud (e.g., the Internet).

While the foregoing is directed to embodiments of the present disclosure, other and further embodiments of the disclosure may be devised without departing from the basic scope thereof, and the scope thereof is determined by the claims that follow.

What is claimed is:

1. A computer implemented method for identifying, based at least in part on a machine learning (ML) model, candidate values to provide to a question answering (QA) system as part of a case, the method comprising:
    receiving a case, wherein the case includes a plurality of documents for evaluation by the QA system;
    evaluating the plurality of documents using natural language processing (NLP) to identify one or more concepts reflected by text content within the plurality of documents in the case, wherein the text content within the plurality of documents includes a first distinct value and a second distinct value of a plurality of distinct values for at least a first one of the concepts, wherein one or more of the plurality of distinct values includes a respective collection of one or more attributes;
    computing by the machine learning (ML) model executing on a processor, a respective confidence score for each of the plurality of distinct values, wherein the ML model comprises a logistical regression model built to compute the scores to select concept values based on a plurality of training cases, wherein each training case provides a plurality of documents and an indication of a preferred value for each concept having multiple values, wherein the preferred value for each concept is determined by:
        assigning a weight to each of the one or more attributes, wherein the one or more attributes include: (i) a date of an observation in the training case, (ii) a decisiveness of language used for the observation, and (iii) an accuracy of a procedure undertaken to make the observation;
        determining whether the one or more attributes meets a previously established relevancy threshold, and i) if the relevancy threshold is met, correlating, based on the assigned weights, a predictive quality of the one or more attributes in relation to a respective concept value to determine the preferred value and ii) if the relevancy threshold is not met, foregoing correlating, based on the assigned weights, a predictive quality of the one or more attribute in relation to a respective concept value to determine the preferred value; and
    selecting, based on the respective confidence scores, the first distinct value of the plurality of distinct values as a candidate value for the first concept to provide to the deep QA system to process the case;
    prior to submitting the case to the QA system, returning at least the candidate value selected for the first concept to present in a user interface; and
    submitting the case to the QA system using at least one selected value.

2. The method of claim 1, wherein the candidate value and the second distinct value are outputted in the user interface, the method further comprising submitting the case and an indication of the candidate value to the QA system for processing.

3. The method of claim 2, wherein the processing comprises generating a treatment recommendation, and wherein the case is an electronic medical record (EMR).

4. The method of claim 1, further comprising:
    receiving a request to view other values from the plurality of distinct values in addition to the candidate value; and
    outputting the candidate value, the second distinct value, and a third distinct value of the plurality of distinct values in the user interface.

5. The method of claim 4, further comprising:
    receiving a selection of one of the second and third distinct values to submit with the case as an indication of the candidate value to the QA system;
    submitting the case to the QA system using the selected one of the second and third distinct values; and
    processing, by the QA system, the case using the selected one of the second and third distinct values as the candidate value for the first concept.

6. A system for identifying, based at least in part on a machine learning (ML) model, candidate values to provide to a question answering (QA) system as part of a case, the system comprising:
    one or more computer processors;
    a memory containing a program which when executed by the one or more computer processors performs an operation, the operation comprising:
    receiving a case, wherein the case includes a plurality of documents for evaluation by the QA system;
    evaluating the plurality of documents using natural language processing (NLP) to identify one or more concepts reflected by text content within the plurality of documents in the case, wherein the text content within the plurality of documents includes a first distinct value and a second distinct value of a plurality of distinct values for at least a first one of the concepts, wherein one or more of the plurality of distinct values includes a respective collection of one or more attributes;
    computing by the machine learning (ML) model, wherein the ML mode is a logical regression model, executed by a processor, a respective confidence score for each of the plurality of distinct values, wherein the ML model is built to compute the scores to select concept values based on a plurality of training cases, wherein each training case provides a plurality of documents and an indication of a preferred value for each concept having multiple values, wherein the preferred value for each concept is determined by:

assigning a weight to each of the one or more attributes, wherein the one or more attributes include: (i) a date of an observation in the training case, (ii) a decisiveness of language used for the observation, and (iii) an accuracy of a procedure undertaken to make the observation;

determining whether the one or more attributes meets a previously established relevancy threshold, and i) if the relevancy threshold is met, correlating, based on the assigned weights, a predictive quality of the one or more attributes in relation to a respective concept value to determine the preferred value and ii) if the relevancy threshold is not met, foregoing correlating, based on the assigned weights, a predictive quality of the one or more attribute in relation to a respective concept value to determine the preferred value; and selecting, based on the respective confidence scores, the first distinct value of the plurality of distinct values as a candidate value for the first concept to provide to the deep QA system to process the case;

prior to submitting the case to the QA system, returning at least the candidate value selected for the first concept to present in a user interface; and submitting the case to the QA system using at least one selected value.

7. The system of claim 6, wherein the candidate value and the second distinct value are outputted in the user interface, the operation further comprising submitting the case and an indication of the candidate value to the QA system for processing.

8. The system of claim 7, wherein the processing comprises generating a treatment recommendation, and wherein the case is an electronic medical record (EMR).

9. The system of claim 6, further comprising:
receiving a request to view other values from the plurality of distinct values in addition to the candidate value; and
outputting the candidate value, the second distinct value, and a third distinct value of the plurality of distinct values in the user interface.

10. The system of claim 9, the operation further comprising:
receiving a selection of one of the second and third distinct values to submit with the case as an indication of the candidate value to the QA system;
submitting the case to the QA system using the selected one of the second and third distinct values; and
processing, by the QA system, the case using the selected one of the second and third distinct values as the candidate value for the first concept.

11. A computer program product, comprising:
a non-transitory computer-readable storage medium having computer-readable program code embodied therewith, the computer-readable program code executable by a processor to perform an operation for identifying, based at least in part on a machine learning (ML) model, candidate values to provide to a question answering (QA) system as part of a case, the operation comprising:
receiving a case, wherein the case includes a plurality of documents for evaluation by the QA system;
evaluating the plurality of documents using natural language processing (NLP) to identify one or more concepts reflected by text content within the plurality of documents in the case, wherein the text content within the plurality of documents includes a first distinct value and a second distinct value of a plurality of distinct values for at least a first one of the concepts, wherein one or more of the plurality of distinct values includes a respective collection of one or more attributes;

computing by the machine learning (ML) model, wherein the ML mode is a logical regression model, executed by a processor, a respective confidence score for each of the plurality of distinct values, wherein the ML model is built to compute the scores to select concept values based on a plurality of training cases, wherein each training case provides a plurality of documents and an indication of a preferred value for each concept having multiple values, wherein the preferred value for each concept is determined by:

assigning a weight to each of the one or more attributes, wherein the one or more attributes include: (i) a date of an observation in the training case, (ii) a decisiveness of language used for the observation, and (iii) an accuracy of a procedure undertaken to make the observation;

determining whether the one or more attributes meets a previously established relevancy threshold, and i) if the relevancy threshold is met, correlating, based on the assigned weights, a predictive quality of the one or more attributes in relation to a respective concept value to determine the preferred value and ii) if the relevancy threshold is not met, foregoing correlating, based on the assigned weights, a predictive quality of the one or more attribute in relation to a respective concept value to determine the preferred value; and selecting, based on the respective confidence scores, the first distinct value of the plurality of distinct values as a candidate value for the first concept to provide to the deep QA system to process the case;

prior to submitting the case to the QA system, returning at least the candidate value selected for the first concept to present in a user interface; and submitting the case to the QA system using at least one selected value.

12. The computer-program product of claim 11, the operation further comprising submitting the case and an indication of the candidate value to the QA system for processing.

13. The computer-program product of claim 12, wherein the processing comprises generating a treatment recommendation, and wherein the case is an electronic medical record (EMR).

14. The computer-program product of claim 11, the operation further comprising:
receiving a request to view other values from the plurality of distinct values in addition to the candidate value; and
outputting the candidate value, the second distinct value, and a third distinct value of the plurality of distinct values in the user interface.

15. The computer-program product of claim 14, the operation further comprising:
receiving a selection of one of the second and third distinct values to submit with the case as an indication of the candidate value to the QA system;
submitting the case to the QA system using the selected one of the second and third distinct values; and
processing, by the QA system, the case using the selected one of the second and third distinct values as the candidate value for the first concept.

* * * * *